US012324627B2

(12) United States Patent
Tsunemichi et al.

(10) Patent No.: US 12,324,627 B2
(45) Date of Patent: Jun. 10, 2025

(54) REFLEXIVE EYE MOVEMENT EVALUATION DEVICE, REFLEXIVE EYE MOVEMENT EVALUATION SYSTEM, AND REFLEXIVE EYE MOVEMENT EVALUATION METHOD

(71) Applicant: Mitsubishi Electric Corporation, Tokyo (JP)

(72) Inventors: Daichi Tsunemichi, Tokyo (JP); Yoshiki Ono, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 71 days.

(21) Appl. No.: 18/288,574

(22) PCT Filed: May 7, 2021

(86) PCT No.: PCT/JP2021/017437
§ 371 (c)(1),
(2) Date: Oct. 27, 2023

(87) PCT Pub. No.: WO2022/234632
PCT Pub. Date: Nov. 10, 2022

(65) Prior Publication Data
US 2024/0206729 A1    Jun. 27, 2024

(51) Int. Cl.
*A61B 3/113*    (2006.01)
*G06T 1/00*    (2006.01)

(52) U.S. Cl.
CPC ............ *A61B 3/113* (2013.01); *G06T 1/0007* (2013.01)

(58) Field of Classification Search
USPC ....................................................... 348/143
See application file for complete search history.

(56) References Cited

U.S. PATENT DOCUMENTS

| 2012/0069301 A1* | 3/2012 | Hirata | A61B 5/4809 |
| | | | 351/209 |
| 2015/0025917 A1* | 1/2015 | Stempora | G02B 27/0093 |
| | | | 705/4 |

(Continued)

FOREIGN PATENT DOCUMENTS

| JP | 5030142 B2 | 9/2012 |
| JP | 6432702 B1 | 12/2018 |

OTHER PUBLICATIONS

International Search Report and Written Opinion mailed on Jun. 29, 2021, received for PCT Application PCT/JP2021/017437, filed on May 7, 2021, 8 pages including English Translation.

*Primary Examiner* — Nigar Chowdhury
(74) *Attorney, Agent, or Firm* — XSENSUS LLP

(57) ABSTRACT

A reflexive eye movement evaluation device is provided for a vehicle, and includes: a reflexive eye movement estimating unit that receives a vehicle exterior video including a visual target of a subject and a vehicle interior video including the subject, the vehicle exterior video and the vehicle interior video being captured by an imaging unit, measures a visual target movement of the subject using the vehicle as a fixed coordinate system from the vehicle exterior video, measures a head movement of the subject from the vehicle interior video, and estimates a reflexive eye movement of the subject; an eye movement measuring unit that measures an eye movement of the subject from the vehicle interior video; and an evaluation value calculating unit that calculates an evaluation value for the reflexive eye movement from the estimated reflexive eye movement and the measured eye movement.

11 Claims, 4 Drawing Sheets

(56) References Cited

U.S. PATENT DOCUMENTS

| | | | |
|---|---|---|---|
| 2015/0212576 A1* | 7/2015 | Ambrus | G06F 3/0482 |
| | | | 345/156 |
| 2018/0299953 A1* | 10/2018 | Selker | G06T 19/006 |
| 2019/0156150 A1* | 5/2019 | Krishnan | G06V 40/70 |
| 2021/0330185 A1* | 10/2021 | Krukowski | G02B 26/0833 |

* cited by examiner

REFLEXIVE EYE MOVEMENT EVALUATION DEVICE, REFLEXIVE EYE MOVEMENT EVALUATION SYSTEM, AND REFLEXIVE EYE MOVEMENT EVALUATION METHOD

CROSS-REFERENCE TO RELATED APPLICATION

This application is based on PCT filing PCT/JP2021/017437, filed May 7, 2021, the entire contents of which are incorporated herein by reference.

TECHNICAL FIELD

The present disclosure relates to a reflexive eye movement evaluating technique.

BACKGROUND ART

A technique for determining whether or not a driver of a vehicle is drowsy has been developed. For example, Patent Literature 1 discloses a technique related to a calculation system including: an imaging unit that is disposed in a mobile object and captures a face of a person in the mobile object; a gyro sensor that is disposed in the mobile object and measures movement data of the mobile object; a first calculating unit that calculates an eye movement of the person using an image of the face captured by the imaging unit; a second calculating unit that calculates a head movement of the person using the movement data of the mobile object measured by the sensor and the image of the face captured by the imaging unit; and a third calculating unit that calculates an index related to awakening of the person using the eye movement calculated by the first calculating unit and the head movement calculated by the second calculating unit.

CITATION LIST

Patent Literature

Patent Literature 1: JP 6432702 B2

SUMMARY OF INVENTION

Technical Problem

However, according to the calculation system of Patent Literature 1, since a movement of another mobile object in an external world of the mobile object is not directly evaluated, there is a problem that a reflexive eye movement cannot be accurately evaluated.

The present disclosure has been made in order to solve such a problem, and an object of the present disclosure is to provide a reflexive eye movement evaluating technique capable of accurately evaluating a reflexive eye movement of a subject in a mobile object.

Solution to Problem

A reflexive eye movement evaluation device according to embodiments of the present disclosure is a reflexive eye movement evaluation device provided for a vehicle, the device including: processing circuitry to receive a vehicle exterior video including a visual target of a subject and a vehicle interior video including the subject, the vehicle exterior video and the vehicle interior video being captured by an imager, to measure a visual target movement of the subject using the vehicle as a fixed coordinate system from the vehicle exterior video, to measure a head movement of the subject from the vehicle interior video, and to estimate a reflexive eye movement of the subject; to measure an eye movement of the subject from the vehicle interior video; and to calculate an evaluation value for the reflexive eye movement from the estimated reflexive eye movement and the measured eye movement.

Advantageous Effects of Invention

A reflexive eye movement evaluation device according to embodiments of the present disclosure can accurately evaluate a reflexive eye movement of a subject in a mobile object.

DESCRIPTION OF EMBODIMENTS

Figure 1:
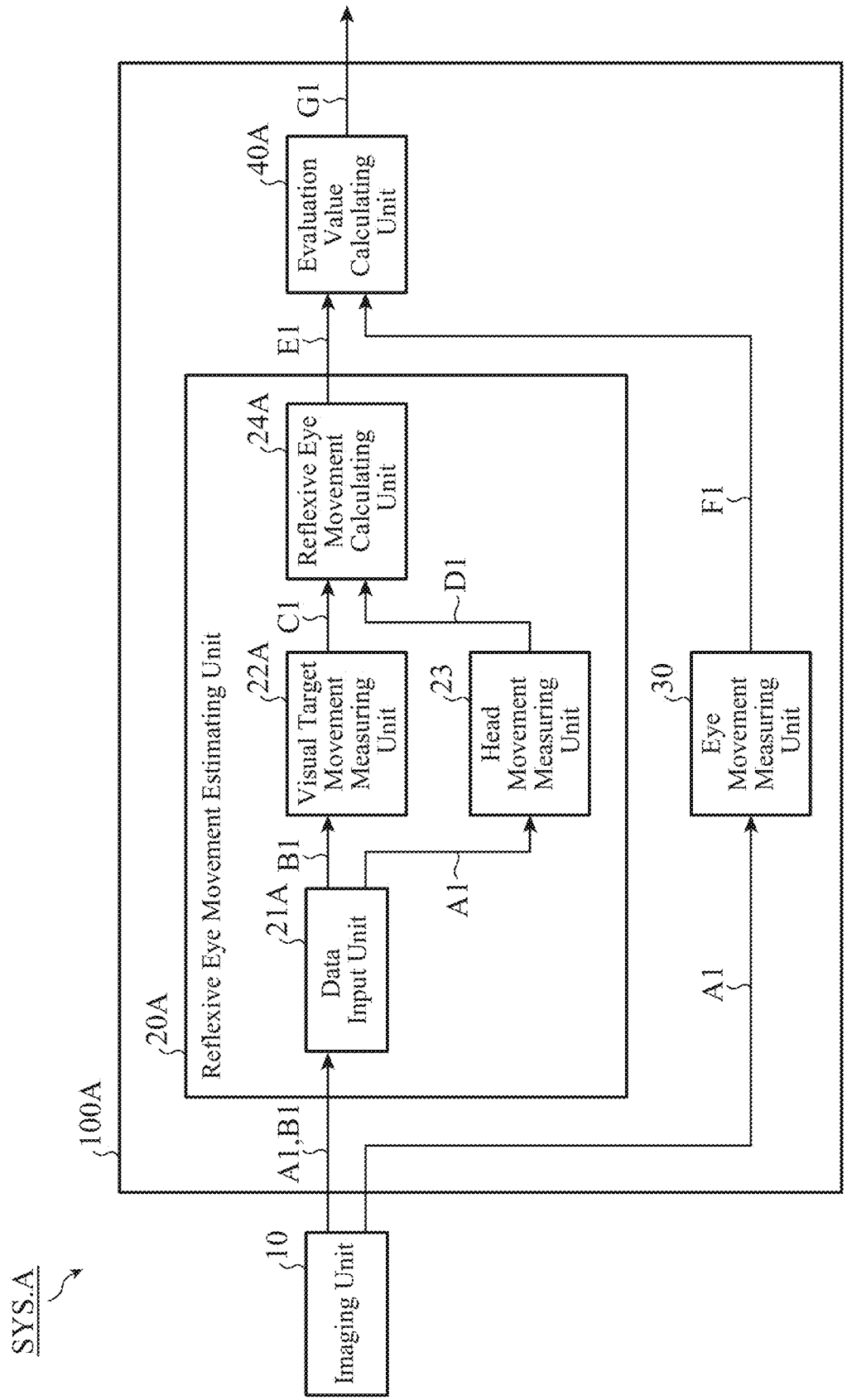
FIG. 1 is a block diagram illustrating a reflexive eye movement evaluation device and a reflexive eye movement evaluation system according to a first embodiment.

Hereinafter, various embodiments in the present disclosure will be described in detail with reference to FIGS. 1 to 5. Note that constituent elements denoted by the same or similar reference numerals throughout the drawings have the same or similar configurations or functions.

First Embodiment

<Configuration>
(Reflexive Eye Movement Evaluation System)

FIG. 1 is a block diagram illustrating a reflexive eye movement evaluation device 100A and a reflexive eye movement evaluation system SYS.A according to a first embodiment of the present disclosure. The reflexive eye movement evaluation system SYS.A is provided for a movable vehicle (not illustrated). The vehicle only needs to be movable, and thus the vehicle may be a two-wheeled vehicle, a three-wheeled vehicle, or a four-wheeled vehicle. As illustrated in FIG. 1, the reflexive eye movement evaluation system SYS.A includes an imaging unit 10 that captures a vehicle exterior video including a visual target at which a subject is gazing and the subject inside a vehicle (typically, a driver of a vehicle), and a reflexive eye movement evaluation device 100A to which a video captured by the imaging unit 10 is input.

Note that, in the present disclosure, the terms "vehicle interior" and "vehicle exterior" are terms distinguished from each other from a viewpoint of whether or not a subject who is actually operating or is planned to operate a vehicle is captured. In other words, the terms "vehicle interior" and "vehicle exterior" are not terms distinguished from each other from a viewpoint of whether or not a space is inside the vehicle. Therefore, for example, in a case where a subject who is actually operating or is planned to operate a vehicle is captured, the term "vehicle interior video" is used. In addition, even in a case where it is difficult to distinguish between a vehicle internal space and a vehicle external space as in a two-wheeled vehicle, the term "vehicle interior video" is used in a case where a subject who is operating a two-wheeled vehicle is captured. The "subject who is planned to operate a vehicle" includes an operator of an automated travel vehicle.

(Imaging Unit)

The imaging unit 10 captures a vehicle interior video A1 including a facial video of a subject inside a vehicle and a vehicle exterior video B1 including a visual target, and outputs the captured vehicle interior video A1 and vehicle exterior video B1. Each of the vehicle interior video A1 and the vehicle exterior video B1 may be captured using a single camera, or may be captured using a stereo camera in order to measure an accurate three-dimensional position. In addition, the vehicle interior video A1 and the vehicle exterior video B1 may be captured as individual videos using different cameras, or may be collectively captured in the same image by a device capable of imaging in a wide range, such as an omnidirectional camera. The imaging unit 10 is connected to a reflexive eye movement estimating unit 20A, and outputs the vehicle interior video A1 and the vehicle exterior video B1 to the reflexive eye movement estimating unit 20A. In addition, the imaging unit 10 is also connected to an eye movement measuring unit 30, and outputs the vehicle interior video A1 to the eye movement measuring unit 30.

(Reflexive Eye Movement Evaluation Device)

The reflexive eye movement evaluation device 100A includes: the reflexive eye movement estimating unit 20A that measures a visual target movement and a head movement and estimates a reflexive eye movement; the eye movement measuring unit 30 that measures an eye movement from a facial video of the vehicle interior video A1; and an evaluation value calculating unit 40A that calculates an evaluation value representing performance of vestibulo-ocular reflex from the estimated reflexive eye movement and the measured eye movement.

(Reflexive Eye Movement Estimating Unit)

The reflexive eye movement estimating unit 20A includes: a data input unit 21A that receives, as inputs, the vehicle interior video A1 and the vehicle exterior video B1 as obtained imaging data, classifies the vehicle interior video A1 and the vehicle exterior video B1 into imaging data necessary for measurement of a visual target movement or imaging data necessary for measurement of a head movement, and outputs the vehicle interior video A1 and the vehicle exterior video B1; a visual target movement measuring unit 22A that measures the visual target movement from the vehicle exterior video B1; a head movement measuring unit 23 that measures the head movement of the subject from the vehicle interior video A1; and a reflexive eye movement calculating unit 24A that estimates a reflexive eye movement of the subject from the visual target movement and the head movement.

(Data Input Unit)

The data input unit 21A classifies the vehicle interior video A1 and the vehicle exterior video B1 into imaging data necessary for measurement of a visual target movement or imaging data necessary for measurement of a head movement, and outputs the vehicle interior video A1 and the vehicle exterior video B1. The data input unit 21A is connected to the visual target movement measuring unit 22A, and outputs the vehicle exterior video B1 to the visual target movement measuring unit 22A. In addition, the data input unit 21A is also connected to the head movement measuring unit 23, and outputs the vehicle interior video A1 to the head movement measuring unit 23.

(Visual Target Movement Measuring Unit)

The visual target movement measuring unit 22A receives, as an input, the vehicle exterior video B1, specifies a visual target region from the vehicle exterior video B1, and outputs a visual target movement measured result C1 that is a result of measuring a visual target movement using the vehicle as a fixed coordinate system. In the specification of the visual target region, for example, the visual target region may be specified by generating a saliency map for estimating a feature to which a person easily directs his/her line of sight in the vehicle exterior video B1, an optical flow indicating a movement amount of an object may be calculated from the vehicle exterior video B1 and a vanishing region in which the optical flow has vanished may be specified as the visual target region, or the visual target region may be specified by combining a result of the saliency map or the optical flow with a result of general object recognition. In this way, by limiting a region at which the subject is gazing or specifying a target object at which the subject is gazing from the entire vehicle exterior video B1, it is possible to measure a movement limited to an object that affects the reflexive eye movement of the subject inside the vehicle. The visual target movement measuring unit 22A is connected to the reflexive eye movement calculating unit 24A, and outputs the visual target movement measured result C1 to the reflexive eye movement calculating unit 24A.

(Head Movement Measuring Unit)

The head movement measuring unit 23 receives, as an input, the vehicle interior video A1, measures a head movement that is a movement of a head of the subject from the vehicle interior video A1 using the vehicle as a fixed coordinate system, and outputs a head movement measured result D1 that is a result of measuring the head movement of the subject. A method for measuring the head movement is described in, for example, Patent Literature 1 and is publicly known, and thus description thereof is omitted. The head movement measuring unit 23 is connected to the reflexive eye movement calculating unit 24A, and outputs the head movement measured result D1 to the reflexive eye movement calculating unit 24A.

(Reflexive Eye Movement Calculating Unit)

The reflexive eye movement calculating unit 24A receives, as inputs, the visual target movement measured result C1 and the head movement measured result D1 using the vehicle as a fixed coordinate system, calculates a reflexive eye movement of the subject from the visual target movement measured result C1 and the head movement measured result D1, and outputs a calculation result as a reflexive eye movement estimating result E1. The reflexive eye movement calculating unit 24A estimates the reflexive eye movement of the subject in the vehicle interior video A1 in the same direction as a direction of the visual target movement and in the opposite direction to a direction of the head movement. The visual target movement perceived by the subject inside the vehicle is a combination of the visual target movement and the head movement using the vehicle as a fixed coordinate system. In order to stabilize a field of view, the reflexive eye movement is a movement that cancels the visual target movement perceived by the subject inside the vehicle. Therefore, an estimated value of the reflexive eye movement is estimated as a movement whose direction is opposite to the direction of the obtained visual target movement. By considering not only the head movement but also the visual target movement, it is possible to estimate the reflexive eye movement depending on a place at which the subject is gazing. The reflexive eye movement calculating unit 24A is connected to the evaluation value calculating unit 40A, and outputs the reflexive eye movement estimating result E1 to the evaluation value calculating unit 40A.

(Eye Movement Measuring Unit)

The eye movement measuring unit 30 receives, as an input, the vehicle interior video A1, measures an eye movement that is an eye movement of the subject from the vehicle interior video A1 using the vehicle as a fixed coordinate system, and outputs an eye movement measured result F1 that is a result of measuring the measured eye movement of the subject. A method for measuring the eye movement is described in, for example, Patent Literature 1 and is publicly known, and thus description thereof is omitted. The eye movement measuring unit 30 is connected to the evaluation value calculating unit 40A, and outputs the eye movement measured result F1 to the evaluation value calculating unit 40A.

(Evaluation Value Calculating Unit)

The evaluation value calculating unit 40A receives, as inputs, the reflexive eye movement estimating result E1 and the eye movement measured result F1, and calculates an evaluation index related to the reflexive eye movement. Examples of the evaluation index include a gain value that is an absolute value ratio of the eye movement of the subject to an estimated value of the reflexive eye movement, and a phase difference, a residual standard deviation, and a periodic difference between a waveform (time-series data) of the estimated value of the reflexive eye movement and a waveform (time-series data) of the eye movement of the subject. Examples of the evaluation index are not limited to these values, and any index may be used as long as the index relates to a correlation between the waveform of the estimated value of the reflexive eye movement and the waveform of the eye movement. In comparing the two pieces of time-series data, it is possible to evaluate similarity between two waveforms by extracting an index related to a correlation between the waveforms. The evaluation value calculating unit 40A calculates at least one index, and outputs an evaluation value obtained from one calculated index or a combination (collection) of two or more calculated indexes as a reflexive eye movement evaluating value G1.

As described above, according to the reflexive eye movement evaluation device 100A and the reflexive eye movement evaluation system SYS.A, the reflexive eye movement of the subject is evaluated using the vehicle exterior video B1 including a visual target at which the subject is gazing, and is therefore accurately evaluated.

Second Embodiment

<Configuration>
(Reflexive Eye Movement Evaluation System)

Figure 2:
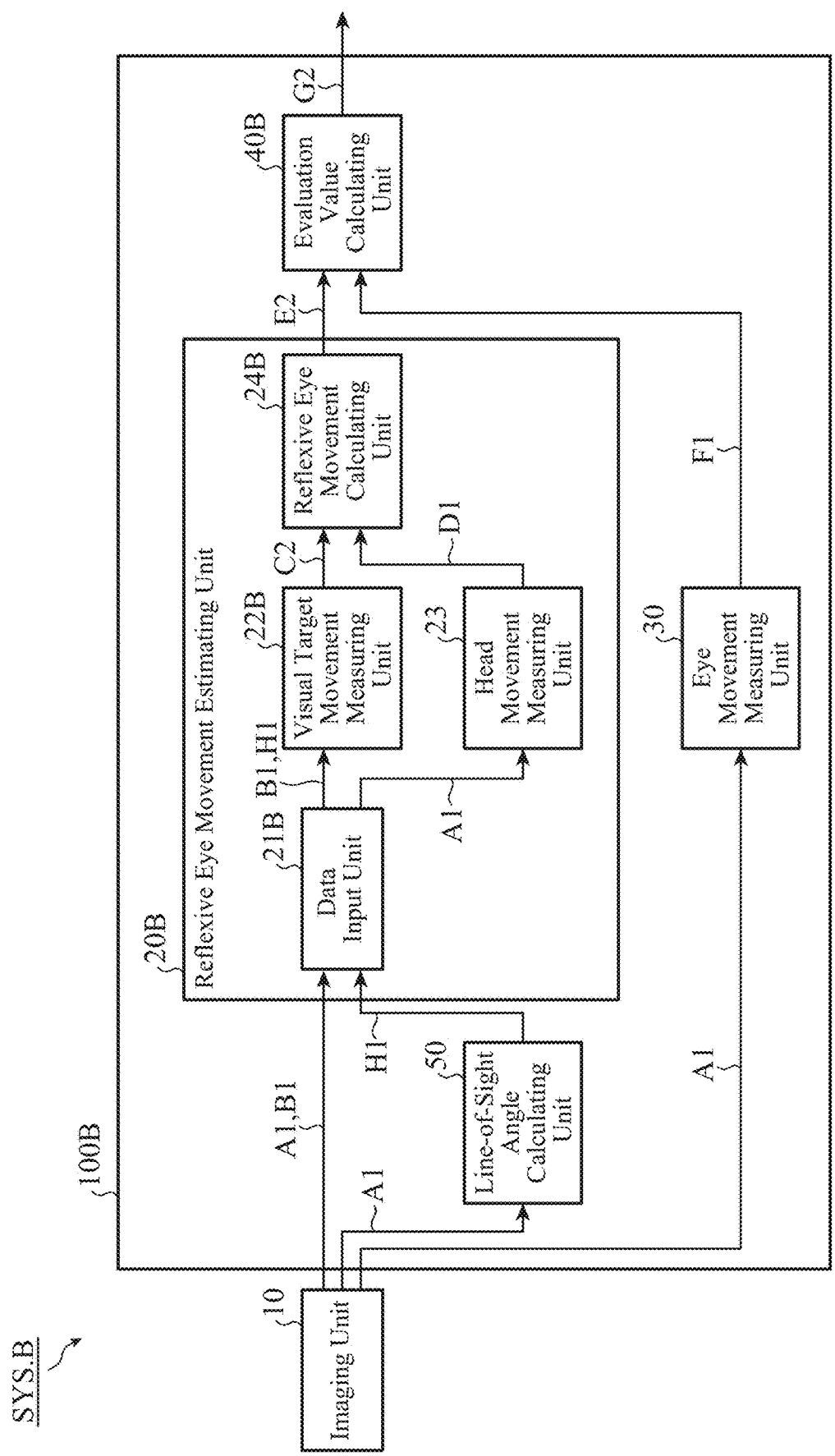
FIG. 2 is a block diagram illustrating a reflexive eye movement evaluation device and a reflexive eye movement evaluation system according to a second embodiment.

FIG. 2 is a block diagram illustrating a reflexive eye movement evaluation device 100B and a reflexive eye movement evaluation system SYS.B according to a second embodiment of the present disclosure. The reflexive eye movement evaluation system SYS.B is provided for a vehicle (not illustrated). As illustrated in FIG. 2, the reflexive eye movement evaluation system SYS.B includes an imaging unit 10 that captures a vehicle exterior video including a visual target and a driver inside a vehicle, and a reflexive eye movement evaluation device 100B to which a video captured by the imaging unit 10 is input.

(Imaging Unit)

The imaging unit 10 captures a vehicle interior video A1 including a facial video of a subject inside a vehicle and a vehicle exterior video B1 including a visual target at which the subject is gazing, and outputs the captured vehicle interior video A1 and vehicle exterior video B1. Each of the vehicle interior video A1 and the vehicle exterior video B1 may be captured using a single camera, or may be captured using a stereo camera in order to measure an accurate three-dimensional position. In addition, the vehicle interior video A1 and the vehicle exterior video B1 may be captured as individual videos using different cameras, or may be collectively captured in the same image by a device capable of imaging in a wide range, such as an omnidirectional camera. The imaging unit 10 is connected to a reflexive eye movement estimating unit 20B, and outputs the vehicle interior video A1 and the vehicle exterior video B1 to the reflexive eye movement estimating unit 20B. In addition, the imaging unit 10 is also connected to an eye movement measuring unit 30, and outputs vehicle interior video A1 to the eye movement measuring unit 30. In addition, the imaging unit 10 is also connected to a line-of-sight angle calculating unit 50, and outputs the vehicle interior video A1 to the line-of-sight angle calculating unit 50.

(Reflexive Eye Movement Evaluation Device)

The reflexive eye movement evaluation device 100B includes: the reflexive eye movement estimating unit 20B that measures a visual target movement and a head movement and estimates a reflexive eye movement; the eye movement measuring unit 30 that measures an eye movement from a facial video of the vehicle interior video A1; an evaluation value calculating unit 40B that calculates an evaluation value representing performance of vestibulo-ocular reflex from the estimated reflexive eye movement and the measured eye movement; and the line-of-sight angle calculating unit 50 that calculates a line-of-sight angle from the facial video of the vehicle interior video A1.

(Line-of-Sight Angle Calculating Unit)

The line-of-sight angle calculating unit 50 receives, as an input, the vehicle interior video A1, calculates a line-of-sight angle of the subject using the vehicle as a fixed coordinate system, and outputs a line-of-sight angle calculating result H1 that is a result of calculating the line-of-sight angle. The line-of-sight angle is an angle formed by a predetermined reference axis, for example, an axis in the front-rear direction of the fixed coordinate system of the vehicle, and a line-of-sight direction of the subject. The line-of-sight angle calculating unit 50 is connected to the reflexive eye movement estimating unit 20B, and outputs the line-of-sight angle calculating result H1 to the reflexive eye movement estimating unit 20B. By calculating the line-of-sight angle of the subject, it is possible to finely specify a visual target outside the vehicle using the result of calculating the line-of-sight angle. Therefore, it is possible to estimate the reflexive eye movement in consideration of a movement of a visual target at which the subject is actually gazing.

(Reflexive Eye Movement Estimating Unit)

The reflexive eye movement estimating unit 20B includes: a data input unit 21B that receives, as inputs, the vehicle interior video A1, the vehicle exterior video B1, and the line-of-sight angle calculating result H1 as obtained imaging data, classifies and outputs imaging data necessary for measurement of a visual target movement and a head movement, and the line-of-sight angle; a visual target movement measuring unit 22B that measures the visual target movement from the vehicle exterior video B1 and the line-of-sight angle calculating result H1; a head movement measuring unit 23 that measures the head movement of the subject from the vehicle interior video A1; and a reflexive eye movement calculating unit 24B that estimates a reflexive eye movement of the subject from the visual target movement and the head movement.

(Data Input Unit)

The data input unit 21B classifies the vehicle interior video A1, the vehicle exterior video B1, and the line-of-sight angle calculating result H1 into data necessary for measurement of a visual target movement or data necessary for measurement of a head movement, and outputs the vehicle interior video A1, the vehicle exterior video B1, or the line-of-sight angle calculating result H1. The data input unit 21B is connected to the visual target movement measuring unit 22B, and outputs the vehicle exterior video B1 and the line-of-sight angle calculating result H1 to the visual target movement measuring unit 22B. In addition, the data input unit 21B is also connected to the head movement measuring unit 23, and outputs the vehicle interior video A1 to the head movement measuring unit 23.

(Visual Target Movement Measuring Unit)

The visual target movement measuring unit 22B receives, as inputs, the vehicle exterior video B1 and the line-of-sight angle calculating result H1, specifies a visual target region from the vehicle exterior video B1 and the line-of-sight angle, and outputs a visual target movement measured result C2 that is a result of measuring a visual target movement using the vehicle as a fixed coordinate system. The visual target region is specified using the line-of-sight angle. Furthermore, the visual target may be specified by combining the line-of-sight angle with a result of general object recognition. The visual target movement measuring unit 22B is connected to the reflexive eye movement calculating unit 24B, and outputs the visual target movement measured result C2 to the reflexive eye movement calculating unit 24B.

(Head Movement Measuring Unit)

The head movement measuring unit 23 receives, as an input, the vehicle interior video A1, measures a head movement that is a movement of a head of the subject from the vehicle interior video A1 using the vehicle as a fixed coordinate system, and outputs a head movement measured result D1 that is a result of measuring the head movement of the subject. The head movement measuring unit 23 is connected to the reflexive eye movement calculating unit 24B, and outputs the head movement measured result D1 to the reflexive eye movement calculating unit 24B.

(Reflexive Eye Movement Calculating Unit)

The reflexive eye movement calculating unit 24B receives, as inputs, the visual target movement measured result C2 and the head movement measured result D1 using the vehicle as a fixed coordinate system, and outputs a reflexive eye movement estimating result E2 that is a result of estimating the reflexive eye movement of the subject. The reflexive eye movement calculating unit 24B estimates a reflexive eye movement of the subject in the vehicle interior video A1 in the same direction as a direction of the visual target movement and in the opposite direction to a direction of the head movement. The visual target movement perceived by the subject inside the vehicle is a combination of the visual target movement and the head movement using the vehicle as a fixed coordinate system. In order to stabilize a field of view, the reflexive eye movement is a movement that cancels the visual target movement perceived by the subject inside the vehicle. Therefore, an estimated value of the reflexive eye movement is estimated as a movement whose direction is opposite to the direction of the obtained visual target movement. By considering not only the head movement but also the visual target movement, it is possible to estimate the reflexive eye movement depending on a place at which the subject is gazing. The reflexive eye movement calculating unit 24B is connected to the evaluation value calculating unit 40B, and outputs the reflexive eye movement estimating result E2 to the evaluation value calculating unit 40B.

(Eye Movement Measuring Unit)

The eye movement measuring unit 30 receives, as an input, the vehicle interior video A1, measures an eye movement that is an eye movement of the subject from the vehicle interior video A1 using the vehicle as a fixed coordinate system, and outputs an eye movement measured result F1 that is a result of measuring the measured eye movement of the subject. The eye movement measuring unit 30 is connected to the evaluation value calculating unit 40B, and outputs the eye movement measured result F1 to the evaluation value calculating unit 40B.

(Evaluation Value Calculating Unit)

The evaluation value calculating unit 40B receives, as inputs, the reflexive eye movement estimating result E2 and the eye movement measured result F1, and calculates an evaluation index related to the reflexive eye movement. Examples of the evaluation index include a gain value that is an absolute value ratio of the eye movement of the subject to an estimated value of the reflexive eye movement, and a phase difference, a residual standard deviation, and a periodic difference between a waveform (time-series data) of the estimated value of the reflexive eye movement and a waveform (time-series data) of the eye movement of the subject. Examples of the evaluation index are not limited to these values, and any index may be used as long as the index relates to a correlation between the waveform of the estimated value of the reflexive eye movement and the waveform of the eye movement. The evaluation value calculating unit 40B calculates at least one index, and outputs an evaluation value obtained from one calculated index or a combination of two or more calculated indexes as a reflexive eye movement evaluating value G2.

Figure 3:
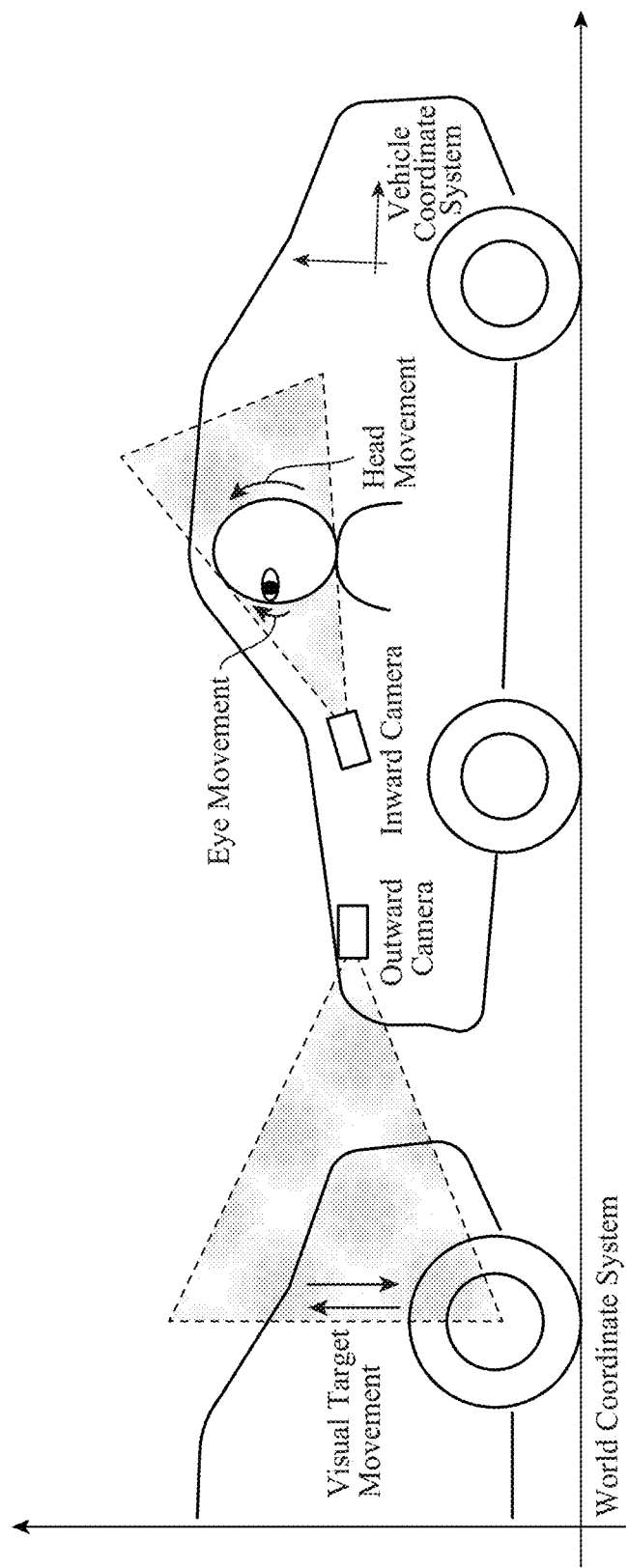
FIG. 3 is a diagram illustrating a difference in a coordinate system considered in the reflexive eye movement evaluation devices or the reflexive eye movement evaluation systems according to the first and second embodiments, and a movement of interest.

FIG. 3 is a diagram illustrating a difference in coordinate systems considered for evaluating the reflexive eye movements related to the first and second embodiments of the present disclosure, and a movement of interest. In FIG. 3, an inward camera is illustrated as a camera that captures the vehicle interior video A1, and an outward camera is illustrated as a camera that captures the vehicle exterior video B1. A world coordinate system in which the gravity direction is defined as the vertical direction and a vehicle coordinate system in which a vehicle is used as a fixed coordinate system can be considered as different coordinate systems when the vehicle itself vibrates.

Since a camera attached to the vehicle and a device that measures vibration are fixed to the vehicle, measured results in the vehicle coordinate system are output.

Meanwhile, in a state where the subject inside the vehicle is gazing at an object outside the vehicle, a visual target movement viewed from the subject is perceived as a result of combining a field-of-view fluctuation due to generation of vibration of the ego vehicle, a field-of-view fluctuation due to generation of a head movement by vehicle vibration, and a movement of a visual target itself. From a vehicle interior video, a head movement and an eye movement of the subject in the vehicle coordinate system can be measured. In addition, from a vehicle exterior video, the field-of-view fluctuation due to vibration of the vehicle and the movement of the visual target itself can be measured as a relative movement viewed from the vehicle coordinate system.

The reflexive eye movement evaluation device 100A or 100B of the present disclosure receives the vehicle exterior video B1 including the visual target captured by the imaging unit 10, and evaluates the reflexive eye movement of the subject. Therefore, the reflexive eye movement evaluation device 100A or 100B considers a movement of a mobile object such as another vehicle outside the vehicle, and therefore can accurately evaluate the reflexive eye movement of the subject.

Figure 4A:
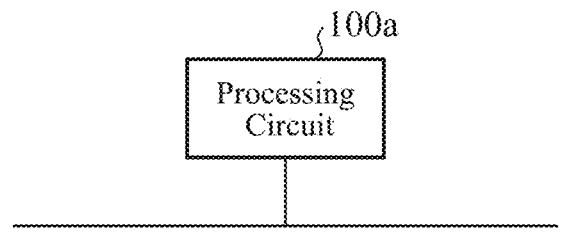
FIG. 4A is a diagram illustrating a configuration example of hardware of each of the reflexive eye movement evaluation devices according to the first and second embodiments.
Figure 4B:
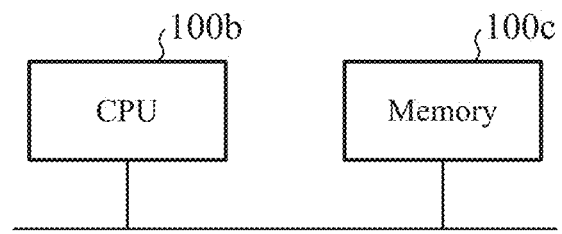
FIG. 4B is a diagram illustrating a configuration example of hardware of each of the reflexive eye movement evaluation devices according to the first and second embodiments.

Next, a configuration example of hardware of each of the reflexive eye movement evaluation devices 100A and 100B will be described with reference to FIGS. 4A and 4B. Functions of the data input unit 21 (21A; 21), the visual target movement measuring unit 22 (22A; 22n), the head movement measuring unit 23, the reflexive eye movement calculating unit 24 (24A; 24n), the eye movement measuring unit 30, the evaluation value calculating unit 40 (40A; 40B) and the line-of-sight angle calculating unit 50 are implemented by a processing circuitry. That is, the reflexive eye movement evaluation devices 100A and 100B each include a processing circuitry for performing various operations such as data reception, visual target movement measurement, head movement measurement, reflexive eye movement calculation, evaluation value calculation, and line-of-sight angle calculation. The processing circuitry may be a dedicated processing circuit 100a as illustrated in FIG. 4A or a CPU 100b that executes a program stored in a memory 100c as illustrated in FIG. 4B.

In a case where the processing circuitry is the dedicated processing circuit 100a, for example, a single circuit, a composite circuit, a programmed processor, a parallel programmed processor, an application specific integrated circuit (ASIC), a field-programmable gate array (FPGA), or a combination thereof corresponds to the dedicated processing circuit 100a. The functions of the data input unit 21 (21A; 21B), the visual target movement measuring unit 22 (22A; 22B), the head movement measuring unit 23, the reflexive eye movement calculating unit 24 (24A; 24B), the eye movement measuring unit 30, the evaluation value calculating unit 40 (40A; 40B) and the line-of-sight angle calculating unit 50 may be implemented by a plurality of different processing circuits, or may be collectively implemented by a single processing circuit.

In a case where the processing circuitry is the CPU 100b, the functions of the data input unit 21 (21A; 21B), the visual target movement measuring unit 22 (22A; 22B), the head movement measuring unit 23, the reflexive eye movement calculating unit 24 (24A; 24B), the eye movement measuring unit 30, the evaluation value calculating unit 40 (40A; 40B) and the line-of-sight angle calculating unit 50 are implemented by software, firmware, or a combination of software and firmware. Software and firmware are each described as a program and stored in the memory 100c. By reading and executing the program stored in the memory, the CPU 100b implements the functions of the units. That is, the memory 100C is disposed for storing programs that cause steps such as a step of performing data reception, a step of performing visual target movement measurement, a step of performing head movement measurement, a step of performing reflexive eye movement calculation, a step of performing evaluation value calculation, and a step of performing line-of-sight angle calculation to be executed as a result. In addition, these programs cause a computer to execute procedures or methods performed by the data input unit 21 (21A; 21B), the visual target movement measuring unit 22 (22A; 22B), the head movement measuring unit 23, the reflexive eye movement calculating unit 24 (24A; 24B), the eye movement measuring unit 30, the evaluation value calculating unit 40 (40A; 40B) and the line-of-sight angle calculating unit 50. Here, examples of the memory 100c include a nonvolatile or volatile semiconductor memory such as a random access memory (RAM), a read-only memory (ROM), a flash memory, an erasable programmable read only memory (EPROM), or an electrically erasable programmable read-only memory (EEPROM), a magnetic disk, a flexible disk, an optical disc, a compact disc, a mini disc, and DVD.

Note that some of the functions of the data input unit 21 (21A; 21B), the visual target movement measuring unit 22 (22A; 22B), the head movement measuring unit 23, the reflexive eye movement calculating unit 24 (24A; 24B), the eye movement measuring unit 30, the evaluation value calculating unit 40 (40A; 40B) and the line-of-sight angle calculating unit 50 may be implemented by dedicated hardware, and some of the functions may be implemented by software or firmware. In this way, the processing circuitry can implement the above-described functions by hardware, software, firmware, or a combination thereof.

(Operation)

Figure 5:
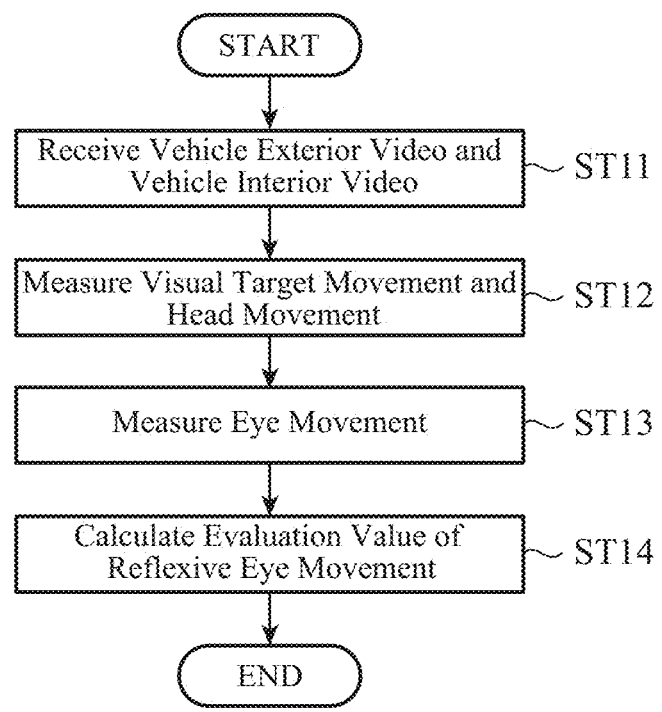
FIG. 5 is a flowchart of a reflexive eye movement evaluation method.

Next, an operation of each of the reflexive eye movement evaluation devices 100A and 100B will be described with reference to FIG. 5.

In step ST11, the reflexive eye movement estimating unit 20 (20A; 20B) receives the vehicle exterior video B1 including a visual target of a subject and the vehicle interior video A1 including the subject, the vehicle exterior video B1 and the vehicle interior video A1 being captured by the imaging unit 10.

In step ST12, the reflexive eye movement estimating unit 20 (20A; 20B) measures a visual target movement from the vehicle exterior video B1, measures a head movement of the subject from the vehicle interior video A1, and estimates a reflexive eye movement of the subject from the measured visual target movement measured result C1 and head movement measured result D1.

When the visual target movement is measured from the vehicle exterior video B1, the line-of-sight angle calculating unit 50 may calculate a line-of-sight angle of the subject from the vehicle interior video A1, and the reflexive eye movement estimating unit 20B may receive the calculated line-of-sight angle calculating result H1 from the line-of-sight angle calculating unit 50 and measure the visual target movement from the vehicle exterior video B1 and the line-of-sight angle calculating result H1. In this case, the reflexive eye movement estimating unit 20B estimates the reflex eye movement of the subject from the visual target movement measured result C2 and the head movement measured result D1.

In step ST13, the eye movement measuring unit 30 measures an eye movement of the subject from the vehicle interior video A1.

In step ST14, the evaluation value calculating unit 40 (40A; 40B) calculates the evaluation value G1 or G2 of the reflexive eye movement from the estimated reflexive eye movement estimating result E1 or E2 and the measured eye movement measured result F1.

SUPPLEMENTARY NOTES

Some of various aspects of the embodiments described above are summarized below.

Supplementary Note 1

A reflexive eye movement evaluation device according to supplementary note 1 is a reflexive eye movement evaluation device (100A; 100B) provided for a vehicle, the reflexive eye movement evaluation device (100A; 100B) including: a reflexive eye movement estimating unit (20A; 20B) that receives a vehicle exterior video (B1) including a visual target of a subject and a vehicle interior video (A1) including the subject, the vehicle exterior video (B1) and the vehicle interior video (A1) being captured by an imaging unit (10), measures a visual target movement of the subject using the vehicle as a fixed coordinate system from the vehicle exterior video, measures a head movement of the subject from the vehicle interior video, and estimates a reflexive eye movement of the subject; an eye movement measuring unit (30) that measures an eye movement of the subject from the vehicle interior video; and an evaluation value calculating unit (40A; 40B) that calculates an evaluation value for the reflexive eye movement from the estimated reflexive eye movement and the measured eye movement.

Supplementary Note 2

A reflexive eye movement evaluation device according to supplementary note 2 is the reflexive eye movement evaluation device according to supplementary note 1, in which the reflexive eye movement estimating unit (20A) includes: a data input unit (21A) that distributes and outputs the vehicle interior video and the vehicle exterior video input from the imaging unit; a visual target movement measuring unit (22A) that measures the visual target movement from the vehicle exterior video; a head movement measuring unit (23) that measures the head movement from the vehicle interior video; and a reflexive eye movement calculating unit (24A) that calculates the reflexive eye movement from the visual target movement and the head movement.

Supplementary Note 3

A reflexive eye movement evaluation device according to supplementary note 3 is the reflexive eye movement evaluation device according to supplementary note 2, in which the visual target movement measuring unit limits a region including the visual target or specifies the visual target by using at least one of a saliency map of the vehicle exterior video, an optical flow of the vehicle exterior video, or object position information detected from the vehicle exterior video by general object recognition.

Supplementary Note 4

A reflexive eye movement evaluation device according to supplementary note 4 is the reflexive eye movement evaluation device according to supplementary note 2, in which the reflexive eye movement calculating unit estimates the reflexive eye movement of the subject in the vehicle interior video in the same direction as a direction of the visual target movement and in the opposite direction to a direction of the head movement.

Supplementary Note 5

A reflexive eye movement evaluation device (100B) according to supplementary note 5 is the reflexive eye movement evaluation device according to supplementary note 1, further including a line-of-sight angle calculating unit (50) that calculates a line-of-sight angle of the subject from the vehicle interior video.

Supplementary Note 6

A reflexive eye movement evaluation device according to supplementary note 6 is the reflexive eye movement evaluation device according to supplementary note 5, in which the reflexive eye movement estimating unit includes: a data input unit (21B) that distributes and outputs the vehicle interior video and the vehicle exterior video input from the imaging unit, and a line-of-sight angle input from the line-of-sight angle calculating unit; a visual target movement measuring unit (22B) that measures the visual target movement from the vehicle exterior video and the line-of-sight angle; a head movement measuring unit (23) that measures the head movement from the vehicle interior video; and a reflexive eye movement calculating unit (24B) that calculates the reflexive eye movement from the visual target movement and the head movement.

Supplementary Note 7

A reflexive eye movement evaluation device according to supplementary note 7 is the reflexive eye movement evaluation device according to supplementary note 6, in which the visual target movement measuring unit limits a region including the visual target or specifies the visual target by using at least one of a saliency map of the vehicle exterior video, an optical flow of the vehicle exterior video, object position information detected from the vehicle exterior video by general object recognition, or the line-of-sight angle.

Supplementary Note 8

A reflexive eye movement evaluation device according to supplementary note 8 is the reflexive eye movement evaluation device according to supplementary note 6, in which the reflexive eye movement calculating unit estimates the reflexive eye movement of the subject in the vehicle interior video in the same direction as a direction of the visual target movement and in the opposite direction to a direction of the head movement.

Supplementary Note 9

A reflexive eye movement evaluation device according to supplementary note 9 is the reflexive eye movement evaluation device according to any one of supplementary notes 1 to 8, in which the evaluation value calculating unit compares time-series data of the estimated reflexive eye movement with time-series data of the measured eye movement, and calculates, as an evaluation value of the reflexive eye movement, a collected value of calculation results regarding at least one index including a gain, a phase difference, a residual standard deviation, or a periodic difference between the two pieces of time-series data.

Supplementary Note 10

A reflexive eye movement evaluation system according to supplementary note 10 includes: the imaging unit; and the reflexive eye movement evaluation device according to any one of supplementary notes 1 to 9.

Supplementary Note 11

A reflexive eye movement evaluation method according to supplementary note 11 is a reflexive eye movement evaluation method performed by a reflexive eye movement evaluation device (100A; 100B), the reflexive eye movement evaluation method including: a step (ST11, ST12) of receiving, by a reflexive eye movement estimating unit (20), a vehicle exterior video including a visual target of a subject and a vehicle interior video including the subject, the vehicle exterior video and the vehicle interior video being captured by an imaging unit, measuring a visual target movement from the vehicle exterior video, measuring a head movement of the subject from the vehicle interior video, and estimating a reflexive eye movement of the subject; a step (ST13) of measuring, by an eye movement measuring unit (23), an eye movement of the subject from the vehicle interior video; and a step (ST14) of calculating, by an evaluation value calculating unit (40), an evaluation value for the reflexive eye movement from the estimated reflexive eye movement and the measured eye movement.

Note that the embodiments can be combined, and each of the embodiments can be appropriately modified or omitted.

INDUSTRIAL APPLICABILITY

The reflexive eye movement evaluation device of the present disclosure can be mounted on a vehicle and used as a part of a driving assistance system.

REFERENCE SIGNS LIST

10: imaging unit, 20: reflexive eye movement estimating unit, 21 (21A; 21B): data input unit, 22 (22A; 22B): visual target movement measuring unit, 23: head movement measuring unit, 24 (24A; 24B): reflexive eye movement calculating unit, 30: eye movement measuring unit, 40 (40A; 40B): evaluation value calculating unit, 50: line-of-sight angle calculating unit, 100 (100A; 100B): reflexive eye movement evaluation device, A1: vehicle interior video, B1: vehicle exterior video, C1: visual target movement measured result, D1: head movement measured result, E1: reflexive eye movement estimating result, F1: eye movement measured result, G1: reflexive eye movement evaluating value, H1: line-of-sight angle calculating result, C2: visual target movement measured result, E2: reflexive eye movement estimating result, G2: reflexive eye movement evaluating value

The invention claimed is:

1. A reflexive eye movement evaluation device provided for a vehicle, the device comprising:
   processing circuitry
   to receive a vehicle exterior video including a visual target of a subject and a vehicle interior video including the subject, the vehicle exterior video and the vehicle interior video being captured by an imager, to measure a visual target movement of the subject using the vehicle as a fixed coordinate system from the vehicle exterior video, to measure a head movement of the subject from the vehicle interior video, and to estimate a reflexive eye movement of the subject;
   to measure an eye movement of the subject from the vehicle interior video; and
   to calculate an evaluation value for the reflexive eye movement from the estimated reflexive eye movement and the measured eye movement.

2. The reflexive eye movement evaluation device according to claim 1, wherein
   the processing circuitry is further configured:
   to distribute and output the vehicle interior video and the vehicle exterior video input from the imager;
   to measure the visual target movement from the vehicle exterior video;
   to measure the head movement from the vehicle interior video; and
   to calculate the reflexive eye movement from the visual target movement and the head movement.

3. The reflexive eye movement evaluation device according to claim 2, wherein
   the processing circuitry is further configured to limit a region including the visual target or specify the visual target by using at least one of a saliency map of the vehicle exterior video, an optical flow of the vehicle exterior video, or object position information detected from the vehicle exterior video by general object recognition.

4. The reflexive eye movement evaluation device according to claim 2, wherein
   the processing circuitry is further configured to estimate the reflexive eye movement of the subject in the vehicle interior video in the same direction as a direction of the visual target movement and in the opposite direction to a direction of the head movement.

5. The reflexive eye movement evaluation device according to claim 1, the processing circuitry is further configured to calculate a line-of-sight angle of the subject from the vehicle interior video.

6. The reflexive eye movement evaluation device according to claim 5, wherein
   the processing circuitry is further configured:
   to distribute and output the vehicle interior video and the vehicle exterior video input from the imager, and the calculated line-of-sight angle;
   to measure the visual target movement from the vehicle exterior video and the line-of-sight angle;
   to measure the head movement from the vehicle interior video; and
   to calculate the reflexive eye movement from the visual target movement and the head movement.

7. The reflexive eye movement evaluation device according to claim 6, wherein
   the processing circuitry is further configured to a region including the visual target or specifies the visual target by using at least one of a saliency map of the vehicle exterior video, an optical flow of the vehicle exterior video, object position information detected from the vehicle exterior video by general object recognition, or the line-of-sight angle.

8. The reflexive eye movement evaluation device according to claim 6, wherein
   the processing circuitry is further configured to estimate the reflexive eye movement of the subject in the vehicle interior video in the same direction as a direction of the visual target movement and in the opposite direction to a direction of the head movement.

9. The reflexive eye movement evaluation device according to claim 1, wherein
the processing circuitry is further configured to compare time-series data of the estimated reflexive eye movement with time-series data of the measured eye movement, and calculates, as an evaluation value of the reflexive eye movement, a collected value of calculation results regarding at least one index including a gain, a phase difference, a residual standard deviation, or a periodic difference between the two pieces of time-series data.

10. A reflexive eye movement evaluation system comprising:
the imager; and
the reflexive eye movement evaluation device according to claim 1.

11. A reflexive eye movement evaluation method performed by a reflexive eye movement evaluation device, the reflexive eye movement evaluation method comprising:
receiving a vehicle exterior video including a visual target of a subject and a vehicle interior video including the subject, the vehicle exterior video and the vehicle interior video being captured by an imager, measuring a visual target movement from the vehicle exterior video, measuring a head movement of the subject from the vehicle interior video, and estimating a reflexive eye movement of the subject;
measuring an eye movement of the subject from the vehicle interior video; and
calculating an evaluation value for the reflexive eye movement from the estimated reflexive eye movement and the measured eye movement.

* * * * *